| United States Patent [19] | [11] Patent Number: 4,874,612 |
|---|---|
| Deasy | [45] Date of Patent: Oct. 17, 1989 |

[54] MULTI-COMPONENT LONG-ACTING MEDICAMENT FORMULATION FOR IMPLANTATION

[75] Inventor: Patrick B. Deasy, Dublin, Ireland

[73] Assignee: Hoechst Aktiengesellschaft, Frankfurt am Main, Fed. Rep. of Germany

[21] Appl. No.: 152,004

[22] Filed: Feb. 3, 1988

[30] Foreign Application Priority Data

Feb. 12, 1987 [DE] Fed. Rep. of Germany ....... 3704275
Mar. 27, 1987 [DE] Fed. Rep. of Germany ....... 3710175

[51] Int. Cl.$^4$ .............................................. A61K 9/22
[52] U.S. Cl. .................................... 424/425; 424/430; 424/487
[58] Field of Search ............................... 424/422–426, 424/430–433, 484–488

[56] References Cited

U.S. PATENT DOCUMENTS 4,293,539  10/1981  Ludwig et al. ...................... 424/19

FOREIGN PATENT DOCUMENTS

| 1196864 | 11/1985 | Canada . |
| 25698 | 3/1981 | European Pat. Off. . |
| 58481 | 8/1982 | European Pat. Off. . |
| 0025698 | 6/1984 | European Pat. Off. . |
| 171907 | 2/1986 | European Pat. Off. . |
| 0179023 | 4/1986 | European Pat. Off. . |
| 1325209 | 8/1973 | United Kingdom . |
| 2059764 | 4/1981 | United Kingdom . |
| WO-A8203174 | 9/1982 | World Int. Prop. O. . |

OTHER PUBLICATIONS

CA103(2): 11404f, Sharon et al.

*Primary Examiner*—Nancy A. B. Swisher
*Attorney, Agent, or Firm*—Finnegan, Henderson, Farabow, Garrett and Dunner

[57] ABSTRACT

Multi-component implants which contain at least two shaped pieces containing active compound, wherein these shaped pieces contain biologically degradable copolymers of lactic acid and glycolic acid with a ratio by weight of lactide to glycolide of 90:10 to 60:40, and wherein there are at least two types of shaped pieces, A and B, type A containing copolymers with a content of lactide which is 5 to 15% by weight lower than in type B, release the active compound over a prolonged period, uniformly or with increasing amount released.

18 Claims, No Drawings

MULTI-COMPONENT LONG-ACTING MEDICAMENT FORMULATION FOR IMPLANTATION

The invention relates to a multi-component long-acting medicament formulation for implantation, which contains biologically degradable shaped pieces containing active compound and shaped pieces containing no active compound.

Pharmaceutical formulations in the form of particles or pellets with controlled release of active compound in which the active compound is present in an intimate mixture with a solid polylactide or another biologically degradable polyester and which are suitable for implantation are already known from British Pat. No. 1,325,209. It is furthermore known, for example from European Patent No. A-25,698, that copolymers of lactic acid and glycolic acid can be used for the preparation of such formulations. The polyesters are slowly degraded and thereby release the active compound over a correspondingly long period of time.

Although medicament formulations of this type are tolerated well, they have the disadvantage that they cannot guarantee uniform and increasing release of the active compound, especially in the event of treatment periods lasting a long time. Rather, the active compound dispersed in the matrix is released in continuously decreasing amounts as a result of the ever decreasing surface due to the gradual degradation of the implant.

Attempts have therefore already been made to achieve a more uniform release of active compound by different distribution of the active compound in the pellet or by admixing additives which can easily be dissolved out. Attempts have also been made to achieve this aim by particular geometric designs of the implant, for example by forming the implant as a thin film or as a hollow fiber. It has been found here, however, that biologically degradable aliphatic polyesters are, even after addition of plasticizers, still so brittle that thin films and hollow fibers are unsuitable for the production of implants which are to be deposited underneath the skin by means of an injection needle with a wide-bore cannula. Such shapes of implants require the use of biologically non-degradable elastomers, such as silicone rubber, if they are not to break even during implantation or immediately after being deposited under the skin.

The invention relates to a multi-component implant which contains at least two shaped pieces containing active compound, wherein these shaped pieces contain biologically degradable copolymers of lactic acid and glycolic acid with a ratio by weight of lactide to glycolide of 90:10 to 60:40, and wherein there are at least two types of shaped pieces, A and B, type A containing copolymers with a content of lactide which is 5 to 15% by weight lower than in type B.

Lactide and glycolide are, in each case, the dimers of lactic and glycolic acid. It is possible to use the pure stereoisomers or mixtures thereof.

Such a combination of types of shaped pieces means that the rate of release of the active compound can be controlled in an optimum manner with uniform or increasing release of the active compound over a prolonged period (up to 12 months), and the disadvantages of the known implants are thus overcome. Furthermore, the implant has the advantage that a so-called burst effect, in which a large amount of active compound is released at the start, is minimied.

The preparation of copolymers of lactic acid and glycolic acid is disclosed in EP-A-26599 and D. L. Wise et al. in Drug Carriers in Biology and Medicine, pages 237–270 (1979), Ed. G. Gregoriadif Academic, Press.

The implant can contain up to 20 shaped pieces containing active compound, in particular 5 to 15 shaped pieces, in particular an odd number of shaped pieces, which are combined in an arrangement in the form of a chain or sandwichlike. It preferably contains 1 to 7 shaped pieces of type B and 2 shaped pieces of type A, there being a shaped piece A located at each of the two ends of the chain.

The shaped pieces required for the medicament formulation according to the invention are in general in the shape of a cylinder with a diameter of 2 to 6 mm, preferably 3 to 4 mm, and a thickness (=height) of 1 to 6 mm, preferably 2 to 4 mm. The total length of the implant can preferably vary between 1 and 4 cm. The shaped pieces are preferably prepared by a procedure in which a mixture containing the active compound, the biologically degradable polymer or copolymer and other suitable additives, such as lubricants, is punched between the flat dies of a tableting press.

The release of active compound from the shaped pieces of the implant can be considerably influenced by various parameters. An increase in the molecular weight of the polyester delays its degradation and the release of the active compound. Within polymers and copolymers of polylactic acid and polyglycolic acid, the rate of degradation increases from poly-L-lactic acid via poly-DL-lactic acid and polylactic/glycolic acid up to polyglycolic acid, at the same molecular weight. An increase in the amount of active compound in the shaped piece increases the rate of release, as does the addition of plasticizers or additives which can easily be dissolved out. The release of active compound can likewise be accelerated by increasing the number of shaped pieces or increasing their surface area. On the other hand, an increase in the pressing pressure or a treatment of the pressed tablets by applying increased temperatures has an inhibiting effect on the release of the active compound.

The average molecular weight ($\overline{M}n$) of the copolymers to be used can vary between 10,000 and 30,000, and the poly-dispersity can vary between 1.5 and 2.5. The shaped pieces A and B can be attached together by adhesive before administration; suitable adhesives for this are those which are biodegradable, such as cyanoacrylates, for example methyl, ethyl or butyl cyanoacrylate.

It is possible by carefully matching the composition of the shaped pieces containing active compound to control the release behavior of the active compound implants in such a way that the duration of release can be varied depending on the nature of the active compound.

In a further embodiment of the invention, it is possible for the implants according to the invention to contain shaped pieces which are of type C, contain no active compound and can be inserted between the shaped pieces containing active compound described above. These shaped pieces can be used to improve the release behavior of the implant over a prolonged period. The shaped pieces of type C are expediently composed of the same copolymers as described for shaped pieces A and B containing active compound.

The copolymers of shaped pieces C can contain 50 to 70% by weight lactide and 50 to 30% by weight glycolide.

The active compound content in the shaped pieces A or B varies between 20 and 80% by weight relative to the weight of the shaped pieces, the active compound content in the shaped pieces A preferably being 5 to 15% by weight lower than in shaped pieces B.

The shaped pieces A, B or C, in particular the shaped pieces C, can contain inert fillers which facilitate the compression of the shaped pieces during their manufacture. Examples of such materials are $MgCO_3$, $MgO$, $CaCO_3$ and $CaHPO_4$. The proportion by weight of these materials in the shaped piece C can be between 30 and 50% by weight.

The implants according to the invention can be used, in particular, in veterinary medicine, but are also suitable for use in human medicine when it is neessary to guarantee a uniform or increasing concentration of medicament in the organism over a prolonged period of time. Such long-acting implants are suitable, in particular, for hormonal disorders, for cancer treatment, for the treatment of infections, circulatory disorders and mental handicaps, and for birth control.

In veterinary medicine, such implants can be used for the treatment of deficiency states (vitamin and trace element deficiencies), chronic infections (long-term administration of anti-infective agents), ecto- and endoparasitoses and impaired function or faulty regulation of endocrine organs (hormone replacement), as well as for uniform release of substances or hormones, especially those which influence growth.

Natural hormones, such as 17 β-estradiol and/or testosterone or their esters, as well as synthetic hormones, such as trenbolone acetate or resorcylic acid lactone (zeranol), significantly influence the growth of calves if they are administered in the form of the multicomponent implant according to the invention. Since the implant can release the active compound over a period of 3 to 12 months, depending on the properties of the shaped pieces selected for this, only a single implantation is necessary for each animal, in contrast with the known implants.

The following active compounds can preferably be employed: steroids or other substances with an anabolic effect, such as trenbolone, zeranol, 17 β-estradiol, testosterone, progesterone or combinations thereof, peptide hormones or substances which release peptide hormones, such as somatotropin, somatotropin-releasing hormone or gonadotropin-releasing hormone.

The finished implants are deposited directly underneath the skin with the aid of a commercially available implantation unit.

The following examples serve to illustrate the invention.

EXAMPLES (a) Preparation of the copolymers of lactic acid and glycolic acid

The commercially available dimers lactide and glycolide, of lactic acid and glycolic acid respectively, were recrystallized three times from ethyl acetate and then dried at 60° C. for 24 hours. For the 80/20 copolymer, 4 g of the L(-)lactide and 1 g of the glycolide were introduced into a predried polymerization tube (Quickfit 7 MF 24-3), together with 0.03% by weight of tin octanoate and 0.01% by weight of lauryl alcohol, both dissolved in hexane. 2.5 g of each of the dimers were used for the 50/50 copolymer.

The reaction vessel was heated under reduced pressure in a silicone oil bath at 200° C. for 4.5 hours, stirring with a magnetic stirrer.

The reaction mixture was then cooled; the resulting copolymer was stored in a desiccator at room temperature.

The copolymer (80% by weight lactide, 20% by weight glycolide) had the following properties: molecular weight $\overline{M}n$: 22,470, polydispersity: 2.26. The copolymers with a different lactide/glycolide content were prepared in the same way. The copolymer with 70% by weight lactide/30% by weight glycolide had a molecular weight $\overline{M}n$: 16,900 and a polydispersity: 1.76.

(b) Manufacture of the shaped pieces

For the shaped pieces containing active compound, 180 mg of 17 β-estradiol were mixed with 120 mg of 80/20 lactide/glycolide copolymer and dissolved in acetone. The solvent was then removed by distillation in vacuo. Tablets were manufactured from the resulting material using a tableting press. The shaped pieces containing no active compound were manufactured analogously.

(c) Biological examples

Implant I

The implant was composed of 5 shaped pieces in the form of cylindrical tablets containing active compound: 3 tablets had a higher content of active compound (type B) and had a diameter of 4 mm and a thickness of 2 mm. The other 2 tablets had the same dimensions but a lower lactide content (type A) and were combined with the tablets of type B in an arrangement in the form of a chain in the sequence: ABBBA.

The tablets B had a copolymer content of 40% by weight with a lactide/glycolide ratio of 80/20 and a content of 17 β-estradiol active compound of 60% by weight. The tablets A were composed of 50% by weight of polymers with a lactide/glycolide ratio of 70/30, and of 50% by weight of 17 β-estradiol.

Implant II

The implant was composed of 9 shaped pieces in the form of cylindrical tablets. Compared with implant I, implant II contained an additional 4 shaped pieces containing no active compound (type C) of the same dimensions as the tablets A or B. The tablets C were inserted between the tablets A and B containing active compound in the following sequence: A-C-B-C-B-C-B-C-A.

The tablets C were composed of 60% by weight of copolymers with a 70/30 lactide/glycolide ratio and of 40% by weight of magnesium carbonate.

In vivo experiment

The rate of release of 17 β-estradiol from the implants I and II described above was determined by determining the blood plasma level before, during and after implantation to castrated male cattle. In addition, the effect on the weight gain was examined by determination of the body weight of the animals before, during and after the implantation.

Material and methods 13 bullocks were divided into 3 groups: two groups of 5 animals each (group I and II) and one group of 3 animals (group III).

Group I (mean weight 145.2 kg) received implant I
Group II (mean weight 144.8 kg) received implant II
Group III (mean weight 141.3 kg) received no implant=control The implantation was carried out using a commercially available applicator. The implant was inserted in the dorsal side of the external ear of the animals.

42 days after the implantation, the implants were removed from two animals from Group I and II, and the estradiol content remaining in the implant was determined by HPLC analysis. 84 days after the implantation, the implants were removed from the remaining 3 animals in each group I and II, and were analyzed.

At defined times before, during and after the implantation blood samples were taken from the tested animals in order to establish the plasma level of estradiol. The estradiol content was determined by a radioimmunological method.

In addition, the experimental animals were weighed at intervals of 2 weeks after the implantation in order to determine the weight gain.

A defined amount of feed was measured out for each animal at each feeding during the experiment, and the intake was monitored.

Results

The amount of estradiol released for implants I and II after 42 and 84 days is shown in Table 1. The plasma level of estradiol is shown in Table 2. The weight gain of the animals is evident from Table 3.

It is clearly evident from the results in Tables 1 to 3 that implants I and II ensure a proportionate release of estradiol over a period of at least 12 weeks, and the weight gain is higher than for the controls.

TABLE 1

| | Release of 17β-estradiol (17β-E) | | | | |
|---|---|---|---|---|---|
| | 17β-E content (mg) per implant before implantation | 17β-E content after | | Release of 17β-E mg/day for | |
| Implant | | 42 days | 84 days | 42 days | 84 days |
| Group I | 78.80/77.06 76.29/76.63/ 75.55 | 72.0/64.0 | 41.4/35.6/ 45.6 | 0.16/0.31 | 0.42/0.49/ 0.39 |
| Group II | 77.94/79.09 79.23/79.47/ 77.96 | 68.5/54.0 | 45.1/49.9 48.3 | 0.22/0.60 | 0.41/0.35/ 0.35 |

TABLE 2

| | | Estradiol plasma levels | | |
|---|---|---|---|---|
| | Days | Group I (pg/ml) | Group II (pg/ml) | Group III (pg/ml) |
| | | (n = 5) | (n = 5) | (n = 3) |
| | −5 | — | 11.7 | 15.8 |
| | −4 | 14.9 | 16.5 | 21.0 |
| Implant administration | 0 | 21.0 | 31.0 | 32.3 |
| | 1 | 92.6 | 83.5 | 16.0 |
| | 2 | 36.0 | 42.6 | 20.7 |
| | 7 | 69.5 | 50.8 | 20.1 |
| | 14 | 36.6 | 62.6 | 21.1 |
| | 21 | 44.8 | 35.0 | 13.4 |
| | 29 | 21.5 | 25.0 | 23.0 |
| | 35 | 22.5 | 12.9 | 10.4 |
| | 42 | 19.5 | 30.9 | 23.0 |
| | | (n = 3) | (n = 3) | |
| | 49 | 25.4 | 32.2 | 22.3 |
| | 56 | 24.0 | 21.0 | — |
| | 63 | 38.0 | 58.3 | 27.7 |
| | 70 | 53.7 | 46.0 | 18.3 |
| | 77 | 68.7 | 58.3 | 25.3 |
| Implant removal | 84 | 160.0 | 125.0 | 26.3 |
| | 85 | 180.0 | 130.0 | — |
| | 86 | 110.0 | 93.3 | — |
| | 90 | 69.0 | 30.0 | 31.3 |

The values relate to pg/ml of plasma and are mean values (X)
n = number of animals

TABLE 3

| | Change in weight (kg) after the implantation | | | | | | |
|---|---|---|---|---|---|---|---|
| Group | 0-2 | 0-4 | 0-6 | 0-8 | 0-10 | 0-12 | week |
| I | 21.4 | 44.2 | 62.3 | 80.0 | 99.3 | 113.3 | |
| II | 21.4 | 45.0 | 57.6 | 69.9 | 85.6 | 105.6 | |
| III Control | 18.3 | 35.0 | 43.3 | 59.0 | 70.3 | 81.3 | |

I claim:

1. A multi-component long-acting implant which contains at least two shaped pieces containing active compound, wherein these shaped pieces contain biologically degradable copolymers of lactic acid and glycolic acid with a ratio by weight of lactide to glycolide of 90:10 to 60:40, and wherein there are at least two types of shaped pieces, A and B, type A containing copolymers with a content olactide which is 5 to 15% by weight lower than in type B.

2. An implant as claimed in claim 1, which contains up to 20 shaped pieces.

3. An implant as claimed in claim 1, which contains an odd number of shaped pieces.

4. An implant as claimed in claim 1, wherein the shaped pieces are arranged in the form of a chain.

5. An implant as claimed in claim 4, wherein a shaped piece of type A is located at both ends of the chain.

6. An implant as claimed in claim 1, which additionally has shaped pieces which contain no active compound and contain copolymers of lactic acid and glycolic acid as claimed in claim 1.

7. An implant as claimed in claim 6, wherein the shaped pieces are arranged in alternating sequence.

8. An implant as claimed in claim 1, wherein the active compound content in the shaped pieces A and B varies between 20 and 80 by weight.

9. An implant as claimed in claim 1, wherein the active compound content in shaped piece A is 5 to 15% by weight lower than in shaped piece B.

10. An implant as claimed in claim 1, which contains an acive compound for human or veterinary medical purposes.

11. An implant as claimed in claim 1, which contains as active compound a natural or synthetic hormone for animals.

12. An implant as claimed in claim 1, wherein the average molecular weight of the copolymers is between 10,000 and 30,000, and the polydispersity of the copolymers is between 1.5 and 2.5.

13. An implant as claimed in claim 1, wherein each of the shaped pieces are in the shape of a cylinder with a diameter of 2 to 6 mm and a thickness of 1 to 6 mm.

14. An implant as claimed in claim 1, wherein the total length of the implant is between 1 and 4 cm.

15. An implant as claimed in claim 1, wherein up to 20 shaped pieces containing active compound are combined in an arrangement in the form of a chain or sandwich-like.

16. An implant as claimed in claim 15, wherein 5 to 15 shaped pieces containing active compound are combined.

17. An implant as claimed in claim 1, wherein 1 to 7 shaped pieces of type B and 2 shaped pieces of type A are combined in a chain, the shaped pieces A located at the two ends of the chain.

18. An implant as claimed in claim 1, wherein 1 to 7 shaped pieces of type B, 2 shaped pieces of type A and shaped pieces which contain no active compound are arranged in alternating sequence in the form of a chain, the shaped pieces A located at the two ends of the chain.

* * * * *

UNITED STATES PATENT AND TRADEMARK OFFICE
CERTIFICATE OF CORRECTION

PATENT NO. : 4,874,612
DATED : October 17, 1989
INVENTOR(S) : PATRICK B. DEASY

It is certified that error appears in the above-identified patent and that said Letters Patent is hereby corrected as shown below:

Claim 1, column 6, line 32, replace "olactide" with --of olactide--.

Claim 8, column 6, line 65, replace "80" with --80%--.

Claim 10, column 7, line 2, replace "acive" with --active--.

Signed and Sealed this

Sixth Day of August, 1991

Attest:

HARRY F. MANBECK, JR.

Attesting Officer

Commissioner of Patents and Trademarks